United States Patent
May et al.

(10) Patent No.: US 7,273,456 B2
(45) Date of Patent: Sep. 25, 2007

(54) METHOD FOR ANALYZING AN EVENT SUCH AS A SURGICAL INTERVENTION ON A BLOOD VESSEL

(75) Inventors: Philippe May, Le Minihic sur Rance (FR); Eric Vicaut, Paris (FR); Jean-Marie Servant, Paris (FR)

(73) Assignee: Universite Paris 7 - Denis Diderot, Paris (FR)

( * ) Notice: Subject to any disclaimer, the term of this patent is extended or adjusted under 35 U.S.C. 154(b) by 0 days.

(21) Appl. No.: 10/432,435

(22) PCT Filed: Jul. 10, 2002

(86) PCT No.: PCT/FR02/02419

§ 371 (c)(1),
(2), (4) Date: Apr. 2, 2004

(87) PCT Pub. No.: WO03/007176

PCT Pub. Date: Jan. 23, 2003

(65) Prior Publication Data

US 2004/0171939 A1 Sep. 2, 2004

(30) Foreign Application Priority Data

Jul. 10, 2001 (FR) .................................. 01 09145

(51) Int. Cl.
*A61B 5/02* (2006.01)
*A61B 5/00* (2006.01)

(52) U.S. Cl. .................. 600/504; 600/300; 600/301

(58) Field of Classification Search .............. 600/300, 600/301, 309, 370, 407, 437, 438, 453–457, 600/504–507, 533, 538–542; 702/12, 19, 702/33, 45–49, 189; 73/1.02, 861, 1.16–1.41, 73/23.24, 53.01, 195–201
See application file for complete search history.

(56) References Cited

U.S. PATENT DOCUMENTS

| | | | |
|---|---|---|---|
| 3,213,682 A * | 10/1965 | Gongwer | 73/170.16 |
| 5,117,689 A * | 6/1992 | Gary | 73/178 R |
| 5,439,483 A | 8/1995 | Duong-Van | |
| 5,471,991 A | 12/1995 | Shinnar | |
| 5,638,823 A | 6/1997 | Akay et al. | |
| 5,957,950 A | 9/1999 | Mockros et al. | |
| 6,135,966 A | 10/2000 | Ko | |
| 6,730,030 B2 * | 5/2004 | Palti | 600/441 |

OTHER PUBLICATIONS

"Traveling Waves in Pipe Flow" Faisst et al. Physical Review Letters vol. 91, No. 22, Nov. 2003.*
"Transition to Turbulence in Particulate Pipe Flow" Matas et al. Physical Review Letters, vol. 90, No. 1, Jan. 2003.*
"Richardson number" Encyclopaedia Britannica. 2005. Encyclopaedia Britannica Online Mar. 20, 2005. http://www.search.eb.com/eb/article?tocid=9063577.*
"Reynolds number" Encylopaedia Britannica 2005. Encyclopaedia Britannica Online Mar. 20, 2005. http://www.search.eb.com/eb/article?tocid=9063389.*
Ruelle et al., Commun. Math. Phys. 20, 167-192 (1971), published by Springer-Verlag, Heidelberg, Germany.
Ruelle et al., Commun. Math. Phys. 23, 343-344 (1971), published by Springer-Verlag, Heidelberg, Germany.
Newhouse et al., Commun. Math. Phys 64, 35-40 (1978), published by Springer-Verlag, Heidelberg, Germany.
May et al., Journal of Surgical Research 99, 53-60 (2001), published by Academic Press, San Diego, CA.
Bräuer et al., Phys. Med. Biol. 44, 1719-1733 (1999), published by Institute of Physics Publishing Ltd., Bristol, United Kingdom.
Aurell et al., Physical Review E, vol. 53, No. 3, 2337-2349, Mar. 1996, published by American Physical Society, College Park MD.
D'Almeida et al., Am. J. Physiol. 268 (Heart Circ. Physiol. 37), H1368, H1371-H1372, 1995, published by The American Physiological Society, Bethesda, MD.
Hutchison, Ultrasound in Med. & Biol., vol. 21, No. 4, 447-458 (1995), published by Elsevier Science Ltd., Elsevier, Inc., New York, NY.
Wagner et al., Am. J. Phsyiol, 268 (Heart Circ. Physiol. 37), H621-H627, 1995, published by American Physiological Society, Bethesday, MD.
Muzy et al., Physical Review Letters, vol. 67, No. 25, 3515-3518, published by The American Physical Society, College Park, MD.
Wolf et al., Physica 16D, 285-317 (1985), published by Elsevier Science Publishers, North-Holland, Amsterdam, The Netherlands.
May, Center for Turbulence Research, Annual Research Briefs 2002, 349-362, published by Stanford University, Stanford, CA.
Vacaut, Drugs 1999, 58 Spec. Issue 1, 1-10, 1999, published by Adis International Limited, Auckland, New Zealand.

Degree of turbulence as a function of degree of stenosis (in rat carotid artery)

Sirieix et al., Critical Care Medicine, 27(10), 2159-2165, Oct. 1999, published by Lippincott Williams & Watkins, Inc., Baltimore, MD.
Mallat et al., Circulation, vol. 96, No. 2, 581-584, Jul. 15, 1997, published by American Heart Association, Inc., Lippincott Williams & Wilkins, Baltimore, MD.
Vicaut, Thérapie 52(5), 429-438 (1997), published by John Libby & Co. Ltd., Eastleigh, United Kingdom.
May et al., Journal of Vascular Research, 39, 21-29 (2002), published by S. Karger AG, Basel, Switzerland.

* cited by examiner

*Primary Examiner*—Charles A. Marmor, II
*Assistant Examiner*—Patricia Mallari
(74) *Attorney, Agent, or Firm*—Buchanan, Ingersoll & Rooney, PC (57) ABSTRACT

A method of analyzing an event comprises the steps consisting in:
  gathering at least one series of measurements of a physical phenomenon associated with the event or likely to be associated therewith;
  from a predetermined mother wavelet $\Psi$ and for at least one value of a predetermined parameter a, determining:
  the partition function $Z(q,a)$ such that:

$$Z(q, a) = \sum_{b_i} |T_\Psi[s](b_i, a)|^q$$

where:
s is a signal representing variation in the measurements of the series as a function of a variable;

$$T_\Psi[s](b,a) = 1/a \int \overline{\Psi}((x-b)/a) s(x) dx$$

where $\overline{\Psi}$ is the complex conjugate of the function $\Psi(x)$ in an orthonormal base; and
$\{(b_i, a)\}_i$ is the set of local maxima in T as a function of a; the spectrum of the function $\tau(q)$ such that:

$Z(q,a) \approx a^{\tau(q)}$ in the limit $a \to 0^+$;
the spectrum of the function $D(h)$ such that:

$$D(h) = \min_q (qh - \tau(q))$$

and an index I(a) depending on said spectrum, which index is calculated by means of a predetermined formula; and comparing the index I(a) or an average of indices I(a) with a predetermined threshold.

11 Claims, 7 Drawing Sheets

Partitioning a singular signal using wavelets of size a centered on the maxima of the modulus of the wavelet transform at scale a

FIG. 3

Signal and maxima lines

PRIOR ART

Degree of turbulence as a function of degree of stenosis (in rat carotid artery)

FIG_7

FIG_8

FIG_9  FIG_10

FIG_11

METHOD FOR ANALYZING AN EVENT SUCH AS A SURGICAL INTERVENTION ON A BLOOD VESSEL

The invention relates to a method and apparatus for analyzing a past or future event in order to determine a quality for said event. For a past event, the result of the analysis makes it possible to take said quality into account for a future action. For a future event, the result enables the event to be better anticipated.

The invention relates more particularly to analyzing the quality of a surgical operation on a blood vessel in the human or animal body in order to determine whether the operation is likely to give rise to particular troubles.

Hemodynamic turbulence is known to facilitate the formation of thromboses (the blood-clot forming process). Conversely, the presence of a thrombus (blood clot) in the vascular bed interferes with hemodynamics and facilitates turbulent behavior. The appearance of such a thrombosis is facilitated during and/or after performing stenosing microsurgical anastomosis (constricting an artery). The study of turbulent hemodynamics is thus a crucial problem in vascular microsurgery.

Knowledge about fluid mechanics shows that the existence of a singularity on the inside surface of the wall of a cylinder in which a stream flows facilitates the appearance of turbulence downstream therefrom. Similarly, the existence of a stenosis (a constriction) in a cylinder in which a stream flows generates turbulence downstream from the stenosis. The appearance of hemodynamic turbulence is facilitated downstream from an arterial stenosis, and this also applies downstream from a microsurgical arterial anastomosis. With an anastomosis, two reasons can be suggested: firstly stenosing power and secondly the presence of microsurgical sutures (for a conventional technique).

At present, there are few medical imaging methods suitable for exploring blood vessels of intermediate size (diameter less than 2 millimeters (mm)), and none of them enables the quality of the blood flow to be investigated. In particular, surgeons have to rely on subjective clinical means only for evaluating the quality of a suture, and that is often highly insufficient for sutures on vessels corresponding to this diameter scale.

Following the precursory work by the mathematician Henri Poincaré at the end of the 19th century, the mathematicians Ruelle et al. have shown that turbulence cannot be analyzed exclusively on the basis of Fourier theory and the algorithms that stem therefrom (D. Ruelle and F. Takens, *On the nature of turbulence*, Commun. Math. Phys. 20: 167-192: 23: 343-344, 1971. See also S. Newhouse, D. Rouelle, and F. Takens, *Occurrence of strange axion A attractors near quasiperiodic flows on $T^m$, $m \geq 3$*, Commun. Math. Phys. 64: 35-40, 1978; and D. Ruelle, *Strange attractors*. The mathematical intelligencer, 2: 126-37, 1980). Turbulence is a non-linear phenomenon and it requires specific mathematical tools to be used when studying non-linear dynamic systems. Studying the non-linearity of a dynamic system provides information about unpredictable changes thereto. The non-linear mathematical tools comprising Lyapunov's greatest exponent and dimension correlation have been used over the last few years mainly in research work in mathematics and fundamental physics and have been applied to characterizing turbulence in the context of studying non-linear dynamic systems.

Wavelet theory has been known for several years and can be used to study turbulent phenomena with precision. The analysis tools derived from wavelet theory have been implemented and improved above all for studying turbulence that is fully developed (turbulence that is super- and hypersonic, explosive, seismic, . . . ). The theoretical approach to analyzing turbulence by time/frequency resolution using the wavelet transform makes it possible to refine analysis of the turbulent flow signal. Nevertheless, no sufficiently advantageous application has yet been proposed for use in studying flows in blood vessels.

Additional information on these topics can be found in the following publications:

P. May, O. Gerbault, C. Arrouvel, M. Revol, J. M. Servant, and E. Vicaut, *Non-linear analysis of arterial oscillated flow in experimental stenosis and microsurgical anastomosis*, Journal of Surgical Research, 97(1), May 2001;

J. C. Van Der Berg, *Wavelets in physics*, Cambridge University Press, 1999, pp. 9-447;

K. Bräuer and M. Hahn, *Non-linear analysis of blood flux in human vessels*, Phys. Med. Biol. 44: 1719-1733, 1999;

H. D. I. Abarbanel, *Analysis of observed chaotic data*, Springer-Verlag, New York, 1996;

E. Aurell, G. Boffetta, A. Crisanti, G. Paladin, and A. Vulpiani, *Predictability in systems with many characteristic times: the case of turbulence, problem in systems with an uncertainty in the evolution law*, Physical Review, E 53: 2337, 1996;

M. S. D'Almeida, C. Gaudi, and D. Lebrec, *Validation of 1- and 2-mm transit-time ultrasound flow probes on mesenteric artery and aorta of rats*, Am. J. Physiol. 268 (Heart Circ physiol 37): H1368-H1372, 1995;

K. J. Hutchison, *Doppler ultrasound spectral shape downstream of significant arterial stenosis in vivo*, Ultrasound in Med. & Biol. 21 (4): 447-458, 1995;

C. D. Wagner and P. B. Persson, *Non-linear chaotic dynamics of arterial blood pressure and renal blood flow*, Am. J. Physiol. 268 (Heart Circ physiol 37): H621-H627, 1995;

W. J. Welch, X. Deng, H. Snellen, and C. S. Wilcox, *Validation of miniature ultrasonic transit-time flow probes for measurement of renal blood flow in rats*, Am. J. Physiol. 268 (Renal Fluid Electrolyte Physiol 37): F175-F178, 1995;

M. V. Wickerhauser, *Adapted wavelet analysis from theory to software*, IEEE Press, 1994;

J. F. Muzy, E. Bacry, A. Arneodo, *Wavelets and multifractal formalism for singular signals: application to turbulence data*, Phys Rev Lett 16; 67(25): 3515-3518, December 1991;

A. Wolf, J. B. Swift, H. L. Swinney, and J. A. Vastano, *Determining Lyapunov exponents form a time series*, Physica D, 16-285-317, 1985;

M. Lesieur, *Turbulence et déterminisme* [Turbulence and determinism], Presses Universitaires de Grenoble, 1998;

P. Abry, *Ondelettes et turbulences* [Wavelets and turbulence], Diderot, Multimedia, 1997; and A. Arneodo, F. Argoul, E. Bacry, J. Elezgaray, J. F. Muzy, *Ondelettes, multifractales et turbulences, de l'ADN aux croissances cristallines* [Wavelets, multifractals, and turbulence in DNA crystal growth], Diderot Editeur, Arts et Sciences, Paris, 1995.

An object of the invention is to improve the analysis of the quality of an event such as the performance of a surgical suture.

To this end, the invention provides a method of analyzing an event, the method comprising the steps consisting in:

gathering at least one series of measurements of a physical phenomenon associated with the event or likely to be associated therewith;

from a predetermined mother wavelet Ψ and for at least one value of a predetermined parameter a, determining:
the partition function Z(q,a) such that:

$$Z(q, a) = \sum_{b_i} |T_\Psi[s](b_i, a)|^q$$

where:
s is a signal representing variation in the measurements of the series as a function of a variable;

$$T_\Psi[s](b,a) = 1/a \int \overline{\Psi}((x-b)/a) s(x) dx$$

where $\overline{\Psi}$ is the complex conjugate of the function Ψ(x) in an orthonormal base; and
$\{(b_i,a)\}_i$ is the set of local maxima in T as a function of a;

the spectrum of the function τ(q) such that:

$Z(q,a) \approx a^{\tau(q)}$ in the limit $a \to 0^+$;

the spectrum of the function D(h) such that:

$$D(h) = \min_q (qh - \tau(q))$$

and an index I(a) depending on said spectrum, which index is calculated by means of a predetermined formula; and comparing the index I(a) or an average of indices I(a) with a predetermined threshold.

This qualitative analysis of the turbulent signal is preferably performed in such a manner that the results of calculating the degree of turbulence are independent of the quantitative parameters constituting the signal (amplitude, frequency, power). This is very advantageous since these quantitative parameters are highly variable in human and veterinary clinical situations.

The method makes it possible to evaluate the quality of the blood flow in a vessel of intermediate size (diameter less than 2 mm). This evaluation is performed by analyzing the degree of turbulence in the blood flow signal. The main applications of this method both during and after an operation are real time detection of:
the existence of a stenosis;
turbulence generated downstream from an anastomosis;
the formation of micro blood clots; and
an assessment of blood viscosity.

This analysis is most advantageous for extra arterial and mini-invasive monitoring of the quality of the blood stream downstream from microvascular anastomoses, thus making it possible to:
detect immediately any technical fault associated with the surgical act;
achieve better reliability in clinical surgery with early detection of any risk of vascular obstruction; and
standardize the measurement of the risk of thrombosis.

The invention integrates a calculation step implemented for example by means of a microprocessor and a software script. This can be integrated in a signal analysis and processing system and/or can be based on an independent unit. The compact and mobile nature of this system makes it possible for it to be used both in a full surgical infrastructure and in the field for operations performed outside in the context of medico-surgical missions.

Because of its purely qualitative nature, this analysis can be applied to other quasiperiodic and turbulent signals that are encountered in other sciences, and at the cost of only minor modifications, for example in the parameters of the software.

Advantageously, the method can present at least one of the following characteristics:
the event is action taken on a duct for receiving a flowing fluid, the values being measurements of a fluid flow rate in the duct, and the variable being time;
the duct forms part of a human or animal body;
the duct is a blood vessel;
the index I(a) is calculated using the formula:

$$I(a) = \frac{y_0}{b+c} + \frac{bc}{y_0(b+c)} + bc - 1$$

in which:

$$y_0 = \max_x D(x) = D(x_0)$$

$b = x_0 - x_{min}$ $c = x_{max} - x_0$ the threshold is 0.35;
I(a) is determined for at least three values of the parameter a;
the values are 6, 7, and 8;
the mother wavelet is of the following type:

$\Psi^{(N)}(x) = (d^N/dx^N) e^{-x^2/2}$ where N is a natural integer;
the mother wavelet is $\Psi^{(1)}$; and
the event is in the past.

The invention also provides apparatus for analyzing an event, the apparatus comprising:
gathering means for gathering measurements of a physical phenomenon associated with the event or likely to be associated therewith; and
determining means for using a predetermined mother wavelet Ψ to determine, for at least one value of a predetermined parameter a:
the partition function Z(q,a) such that:

$$Z(q, a) = \sum_{b_i} |T_\Psi[s](b_i, a)|^q$$

where:
s is a signal representing variation in the measurements of the series as a function of a variable such as time;

$$T_\Psi[s](b,a) = 1/a \int \overline{\Psi}((x-b)/a) s(x) dx$$

where $\overline{\Psi}$ is the complex conjugate of the function Ψ(x) in an orthonormal base; and {(b$_i$,a)}$_i$ is the set of local maxima in T as a function of a;

the spectrum of the function τ(q) such that:

$$Z(q,a) \approx a^{\tau(q)} \text{ in the limit } a \to 0^+;$$

the spectrum of the function D(h) such that:

$$D(h) = \min_q (qh - \tau(q))$$

and an index I(a) depending on said spectrum, which index is calculated by means of a predetermined formula.

Preferably, the apparatus includes means for comparing the index I(a) or an average of indices I(a) with a predetermined threshold.

Other characteristics and advantages of the invention appear further from the following description of a preferred embodiment given by way of non-limiting example. In the accompanying drawings:

FIG. 2 shows a singular signal partitioned using wavelets of the same size a centered on the maxima of the modulus of the wavelet transform at scale a;

Figure 1:
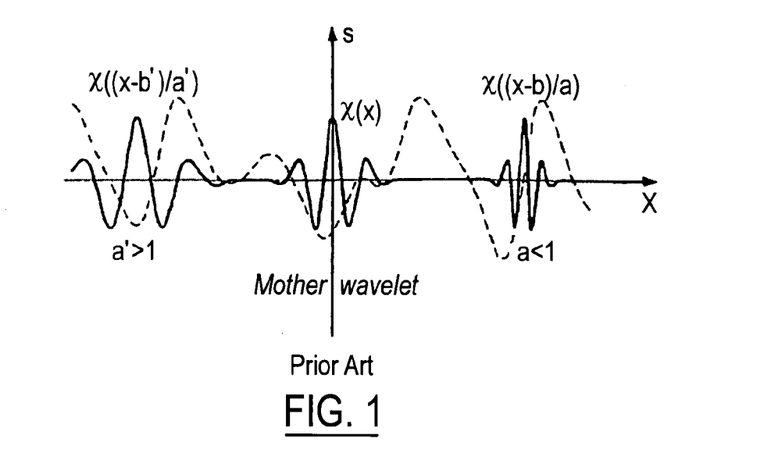
FIG. 1 is a graph showing a signal and a family of wavelets enabling it to be analyzed.
Figure 2:
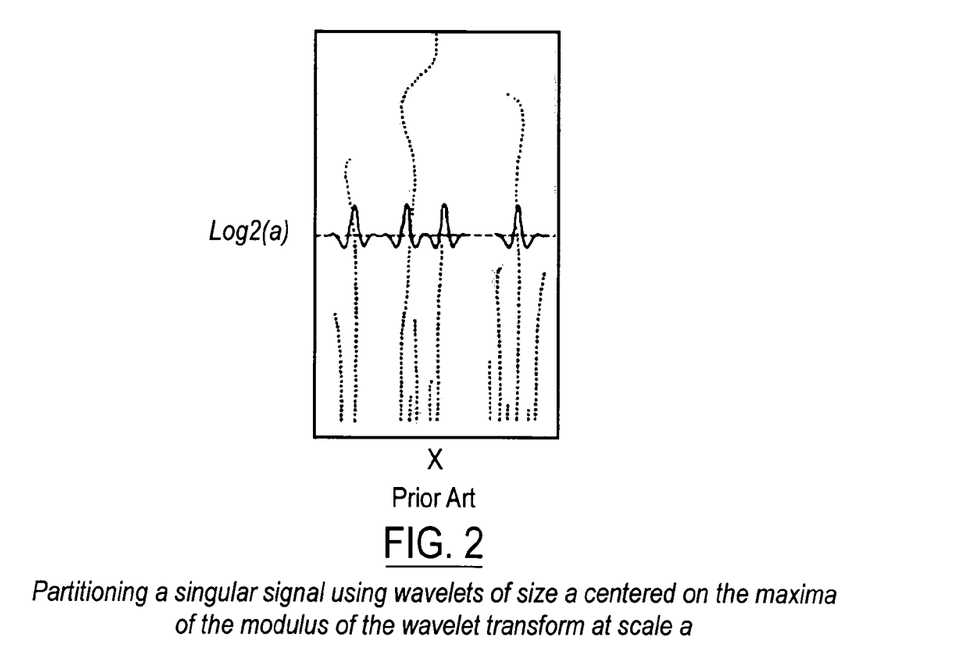
Figure 4:
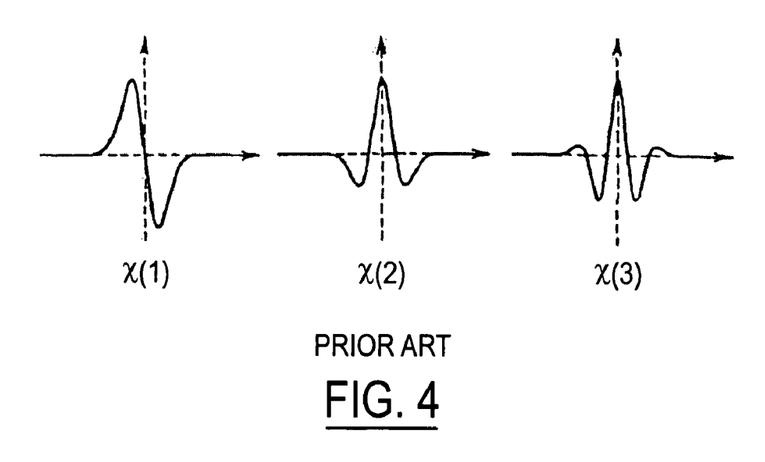
FIG. 4 shows the graphs of three functions of a family of wavelets used in implementing the method of the invention.

This description begins with some general points concerning multiresolution analysis and processing of singularities in a turbulent signal by means of wavelets. A large portion of this information is taken from the following work: A. Arneodo, F. Argoul, E. Bacry, J. Elezgaray, J. F. Muzy, *Ondelettes, multifractales et turbulences, de l'ADN aux croissances cristallines*, Diderot Editeur, Arts et Sciences, Paris, 1995. Indeed FIGS. 1, 2, and 4 are taken from that work.

If it is desired to obtain a representation of the frequency properties of a signal locally in time, it is appropriate to analyze the signal by means of signals that are themselves local in time and in frequency. These signals that are local in time and in frequency are grouped together in families of wavelets.

Wavelets are an extension of Fourier analysis. Like the Fourier transform, the wavelet transform is based on transforming a signal into numbers known as "coefficients" which can be recorded, analyzed, manipulated, transmitted, or used for reconstructing the original signal. These coefficients specify how the analyzing function (the wavelets) should be modified in order to obtain curves which, on being assembled together, reproduce the original signal.

A signal is reconstructed from its wavelet transform by adding wavelets of different sizes. In principle, coefficients are calculated in the same manner as for the Fourier transform: the signal and the analyzing function (wavelet) are multiplied together and the integer of the product is calculated.

The wavelet transform makes use of the possibility of compressing or stretching wavelets in order to change their analysis frequency, and in the wavelet transform the sinewave of the Fourier transform is replaced by a family of translations and dilations of a single function, a wavelet. The translation and dilation parameters are the two arguments of the wavelet transform.

In order to determine the singularity spectrum (turbulence) of the flow signal, the wavelet transform modulus maximum (WTMM) method of calculation is used. This method mainly comprises the following two steps:

1) calculating the wavelet transform of the signal and calculating local maxima in its modulus; and 2) calculating partition functions, measuring exponents τ(q), and performing the Legendre transform. This method serves to obtain the spectrum D(h) of the singularities of the signal.

To the above method which is conventional, the invention adds an additional calculation step: analyzing the spectrum D(h) of signal singularities. This last step includes determining a dimensionless singularity index I which is specific to each analyzed signal.

1) Calculating the Wavelet Transform of the Signal and Calculating Local Maxima in its Modulus.

In dashed lines, FIG. 1 shows a signal s(x), and in continuous lines it shows a mother wavelet Ψ(x) of L²(R) (Hilbert space) together with two associated wavelets Ψ$_{b,a}$, one corresponding to an expansion (a>1) and the other corresponding to a contraction (a<1).

∫Ψ(x)dx=0 is referred to as the analyzing wavelet.

A Hilbert space is a vector space provided with a product that is scalar and complete for the associated norm.

Starting from a mother wavelet Ψ(x) it is possible to create a Hilbert base of L²(R) by translating and dilating the mother wavelet:

$$\Psi_{j,k}(x) = 2^{j/2}\Psi(2^j x - k)$$

where:

j and k belong to z and are respectively scale and position;

Z is an orthonormal base of L²(2) i.e. ∀f∈L²(R), f=Σλ$_j$, $_k$Ψ$_{j,k}$.

The wavelet transform of a signal s(x) consists in breaking up the signal s(x) into the form of a linear combination of wavelets Ψ$_{b,a}$ and calculating respective wavelet coefficients therefrom. This wavelet transform T$_\Psi$ is a function of two variables a and b which "evaluate" the pertinence of using the wavelet Ψ$_{b,a}$ in describing the signal s(x).

The idea is thus to project the signal s(x) onto a function space of limited-time media (wavelets) so as to be able to study what happens locally.

The signal s(x) is projected onto a family of functions having an average value of zero (wavelets), which are derived from an individual function (the mother wavelet) by translations and dilations.

This is known as the continuous wavelet transform (CWT) and is used in the WTMM method for calculating the set of wavelet coefficients. Each wavelet coefficient is the result of calculating the integral between a daughter wavelet $\Psi_{b,a}$ and the signal s(x) analyzed at scale a. Calculating this integral is equivalent to taking a scalar product between the matrix of the daughter wavelet $\Psi_{b,a}$ and that of the signal s(x) at scale a.

This set of coefficients is made easier to calculate when the wavelet base is orthonormal.

The continuous wavelet transform is defined as follows:

$$T_\Psi[s](b,a) = 1/a \int \overline{\Psi}((x-b)/a) s(x) dx$$

b: position (or time) parameter and varies in R;
a: scale (or frequency) parameter and is strictly positive;
$\overline{\Psi}$: complex conjugate of the function $\Psi(x)$ in an orthonormal base.

The closer the "similarity" between the wavelet $\Psi_{b,a}$ and the signal s(x) locally around the point x=b, the greater the absolute value of the wavelet transform $T_\Psi[s]$ at the point (b,a).

Wavelets are commonly referred to as a "mathematical microscope" because of their ability to dissect a signal. This dissection serves to show up singularities in the signal, which in the present context become a support for turbulence.

The appropriate exponent which makes it possible to "measure" the strength of the singularity of a signal at a point $x_0$ is the Hölder exponent $h(x_0)$. This exponent is defined as being the greatest exponent h for which there exists a polynomial $P_n$ of degree n and a constant C satisfying:

$$|s(x) - P_n(x - x_0)| \leq C|x - x_0|^h \quad (x \to x_0)$$

The spectrum of singularities of interest is thus the spectrum of Hölder exponents, i.e. the function D(h) defined by:

$$D(h) = d_F(\{x_0 \in R / h(x_0) = h\})$$

where $d_F$ represents the fractal dimension.

The partition associated with the new partition function that is to be defined must thus satisfy two conditions: it must cover only singular portions of the signal, and each element of the partition must constitute a local "measurement" of the Hölder exponent.

Figure 3:
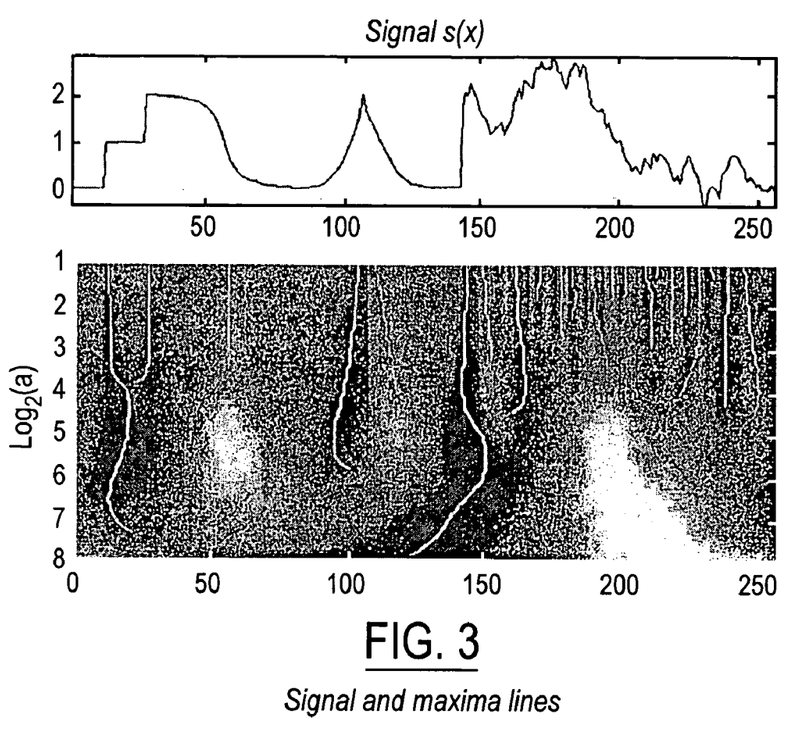
FIG. 3 shows two graphs of a signal and the associated maxima lines.

The maxima of the modulus of the wavelet transform appear to satisfy these two requirements very well. Firstly, at a given scale a, a maximum local to the position $x_0$ represents a sudden change in the signal, and thus represents behavior that is singular. Furthermore, the behavior of the wavelet transform along a line of maxima pointing towards $x_0$ behaves like $a^{h(x_0)}$ as a tends to zero. It is thus possible to partition the signal at a given scale a with wavelets of size a and positioned at locations where the local maxima in the modulus appear.

FIGS. 2 and 3 show such a partition. By way of example, FIG. 2 shows a partition of a singular signal using wavelets of the same size a centered on the maxima of the modulus of the wavelet transform at scale a. FIG. 3 shows two graphs, one representing a signal and the other the associated lines of maxima.

2) Calculating Partition Functions, Measuring Exponents $\tau(q)$, and Performing the Legendre Transform.

The partition function is defined by:

$$Z(q, a) = \sum_{b_i} |T_\Psi[s](b_i, a)|^q$$

where:
$T_\Psi[s]$ is the wavelet transform of a signal s(x);
$\{(b_i, a)\}_i$ is the set of local maxima at scale a; and q belongs to R.

The exponent $\tau(q)$ is defined as follows:

$$Z(q,a) \approx a^{\tau(q)} \text{ in the limit } a \to 0^+$$

The canonical approach consists in calculating the spectrum D(h) of the singularities of the signal s as the Legendre transform of the function $\tau(q)$:

$$D(h) = \min_q (qh - \tau(q))$$

Specifically, the analyzing wavelet selected for analyzing the flow signal belongs to successive derivatives of the Gaussian function, which are written as follows:

$$\Psi^{(N)}(x) = (d^N/dx^N) e^{-x^2/2}$$

where N is a natural integer.

These functions present the advantage of being well localized both in ordinary space and in Fourier space. Three of these functions are shown in FIG. 4 with N equal to 1, 2, and 4 respectively. In this case, $\Psi^{(1)}$ is selected for all of the analyses. Nevertheless, the algorithm used can also make use of other derivatives of Gaussian functions in order to match the signal under investigation more closely. It is even possible to use analyzing functions of some other type.

Figure 5:
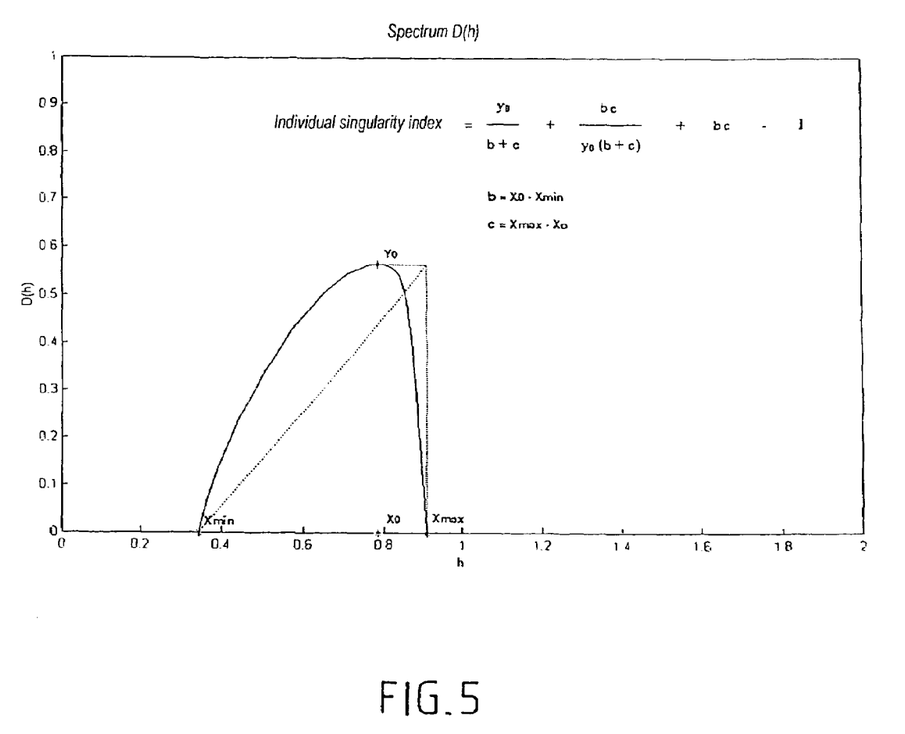
FIG. 5 is a graph of the function D(h) used in implementing the invention and shows the geometrical construction representative of calculating the index I(a)

With reference to FIG. 5, the individual singularity index of the signal is calculated in this case by applying the following formula for each value of a:

$$I(a) = \frac{y_0}{b + c} + \frac{bc}{y_0(b + c)} + bc - 1$$

in which $$y_0 = \max_x D(x) = D(x_0)$$

$$b = x_0 - x_{min}$$

$$c = x_{max} - x_0$$

This index I(a) is calculated for the function D(h) associated with each value of the parameter a. The index I(a) takes account of the maximum $y_0$ of the function D(h), of the width $(x_{max} - x_{min})$ of the base of its spectrum along the abscissa axis, and of the more or less sudden character of the falling front of this spectrum. As a result, the index enables the shape of the spectrum to be characterized closely, and thus to be summarized.

The individual singularity index is calculated on three scales, i.e. for three values of the parameter a which are predetermined experimentally, and which are advantageously as follows:

a=6; a=7; a=8

The arithmetic mean of these results I(a) constitutes the overall singularity index I of the signal s under analysis. In this case:

$$I = [I(6) + I(7) + I(8)]/3$$

Figure 6:
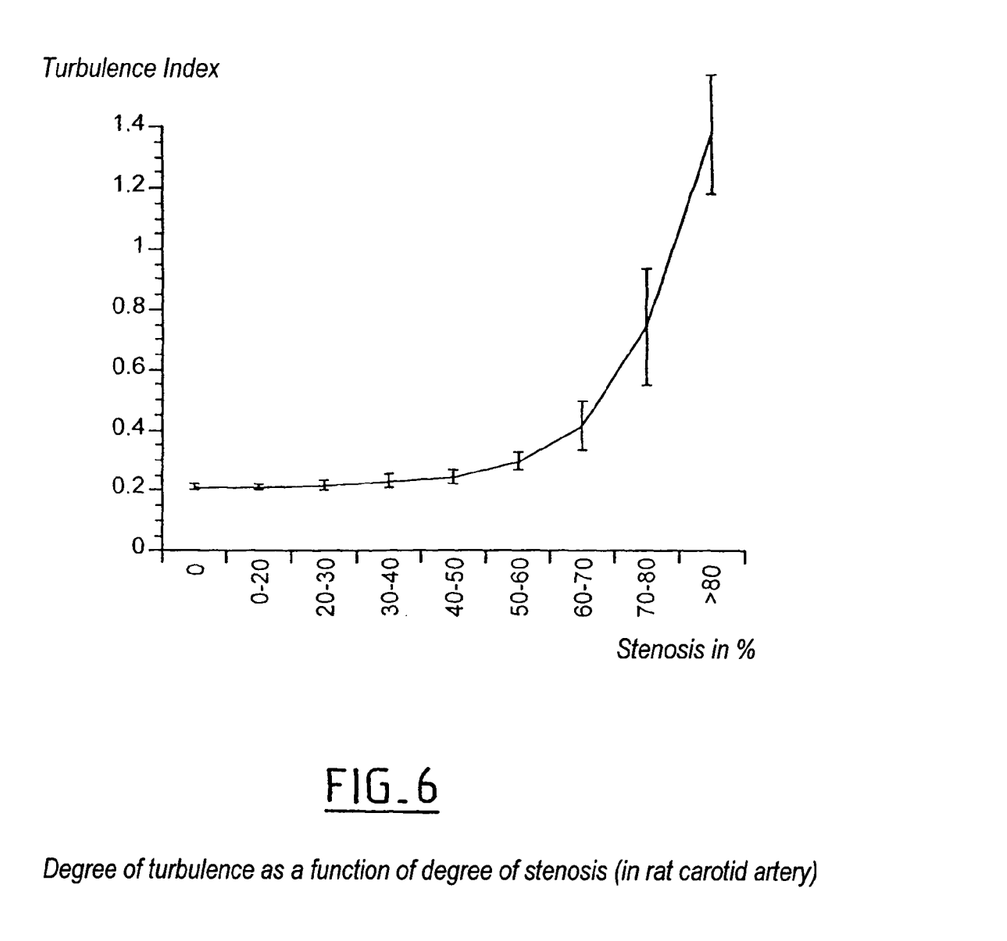
FIG. 6 is a graph showing in vivo variation in the degree of turbulence as a function of the degree of stenosis of a rat carotid artery.

This singularity index has made it possible to establish the curve shown in FIG. 6 where the index is plotted up the ordinate. FIG. 6 is a graph showing how the degree of turbulence I varies in vivo as a function of the degree of stenosis in a rat carotid artery. It illustrates how the invention can be applied in in vivo experimental conditions on the rat. It shows a close experimental correlation (p<0.001) between the degree of arterial stenosis and the level of hemodynamic turbulence downstream therefrom when using the present method of analyzing the signal. This curve confirms that the index is pertinent. This particular rat artery (diameter less than 2 mm) was selected because it is straight and because of the absence of collateral arteries. The oscillating arterial flow signal was recorded using a flow rate probe having the reference No. 1V and sold by Transonic System, Inc., together with a flow meter referenced T206 sold by Transonic System, Inc., said flow meter being coupled to an analog acquisition system referenced MP30 sold by Biopac System, Inc., with the signal delivered by the flow meter being converted into a digital signal.

To distinguish between non-thrombosis generating hemodynamic flow and thrombosis-generating-hemodynamic flow, and in agreement with the results shown in FIG. 6, it is advantageous to select a limit value for the singularity index that is equal to 0.35. Given the variations in experimental measurements, this value provides a satisfactory level of security. However, it could easily be modified in the decision-making algorithm. Thus, so long as the index is less than 0.35, turbulence in the blood vessel should not be considered as being abnormal, otherwise it should be considered as being abnormal. In which case, the quality of the surgery needs to be verified and additional examinations and new surgery might need to be performed, either immediately or later on.

In the context of the invention, an important step in this analysis of the flow rate signal (which varies from being almost periodic towards being turbulent) lies in calculating the index I which is a magnitude that serves to characterize the degree of turbulence. This magnitude is dimensionless. It can be obtained by writing a calculating algorithm and a software script, for example in the software environment sold under the name Matlab. The software used in the invention is easily transferred into the C language. The C language can then be compiled into assembler language and then loaded into the memory of a microprocessor (DSP, microcontroller, . . . ).

Figure 7:
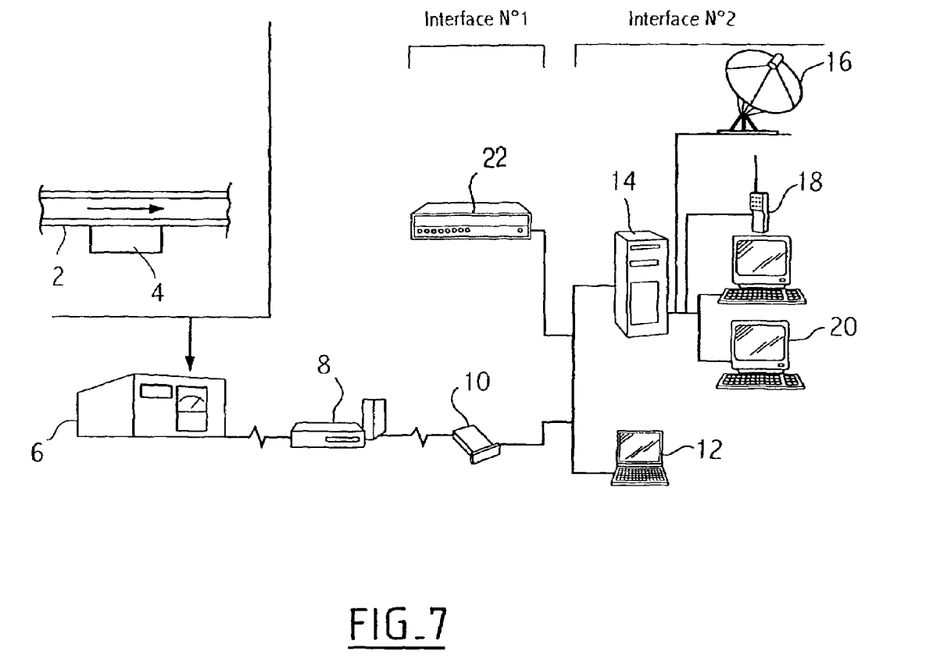
FIG. 7 shows how apparatus of the invention can be arranged for implementation of the invention.

FIG. 7 shows a preferred embodiment of apparatus of the invention enabling the method to be implemented.

The apparatus comprises means for measuring blood flow rate at various instants in a blood vessel 2. These means comprise at least one sensor or probe 4 of conventional type placed in the vicinity of the blood vessel and constituted in various manners that are themselves known (Doppler probe, . . . ). The probe 4 may be fixed to the end of an arm of a microsurgical robot.

The values obtained from the probe form a one-dimensional signal. The method of the invention enables a lightweight calculation method to be implemented using the wavelet transform. With this tool, it is possible, for example, to make do with a signal made up of 2048 points. In accordance with Shannon's theorem, a sampling frequency of 500 hertz (Hz) is sufficient for recording the flow rate signal when implementing the invention on the rat.

Thereafter, the apparatus comprises parameterizable means for acquiring the signal (sound, acoustic, . . . ) which also perform digital encoding. These means forming interface No. 1 may comprise, for example, a flow meter 6 connected to the probe 4 in order to receive information therefrom, an analog-to-digital converter 8 connected to the flow meter 6, and an acquisition card 10 having a microprocessor and assembler code connected to the converter. The card performs multiresolution analysis and processing using wavelets on the signal by implementing the modified WTMM method. These processor means may be arranged to enable the family of analyzing wavelets to be selected in parameterizable manner. They perform the following:

calculating the wavelet transform of the signal and calculating local maxima in its modulus;
calculating partition functions, measuring the exponent $\tau(q)$, and performing the Legendre transform;
analyzing the spectrum of signal singularities; and
calculating the singularity index.

These processor means are programmed to output the singularity index I of the signal together with the signal s and its detailed analysis.

The card 10 comprises in a form integrated in a logic circuit (microprocessor, DSP, microcontroller, . . . ) a compiled version of the code coming from the algorithm for processing and analyzing the signal in real time. The logic circuit then compares the result (the numerical value of the index I) with a parameterizable scale of values for the degree of turbulence stored in read only memory (ROM). The first measurement value is referenced in order to be compared with subsequent values (monitoring the risk of thrombosis).

Thereafter, the apparatus comprises processor means forming interface No. 2, e.g. in the form of a portable computer 12 or an office computer 14 serving to provide a real time representation of the level of turbulence. For this purpose, these means comprise a monitor and a graphics interface and/or an auxiliary unit having a scale of colored light-emitting diodes (LEDs) and/or a proportional sound-generating device. The (portable or office) computer may constitute a support for the signal processing and analyzing card and a support for communications protocols between the two interfaces. These protocols are preferably adapted to being configured as a network (serial, IR, laser, Ethernet, Internet (TCP/IP, IPX, NT, Novel, . . . ), wireless, telemetry, . . . ). Thus, under certain circumstances, the results of the analysis may be transmitted by satellite using appropriate means 16, by wireless telephony 18, by radio waves, or over a cable network 20.

The apparatus may further comprise a third interface providing feedback to the dynamic system in operation, such as a therapeutic pump, a motor, a hydraulic pump, a pipeline (with flow rate being adjusted by means of valves), . . . . The method of the invention can thus be implemented while surgery is taking place so as to be able to act immediately on the blood vessel as a function of the result of turbulence analysis.

Alternatively or additionally, the apparatus may include an integrated unit 22 performing the steps of acquisition, calculation, and display, e.g. by means of a strip of LEDs giving a signal proportional to the value of the resulting index. LEDs of two or more different colors may be used to constitute the strip so as to visualize one or more threshold values directly. For example, a first series of green LEDs may light up so long as the value is below 0.35, with the quantity of LEDs being proportional to the value. If the value exceeds the threshold, then other LEDs that are red in color light up, with the number of lighted LEDs being proportional to the value and following on from the green LEDs.

The invention is implemented as follows. It is assumed that it is desired to verify that surgery on a blood vessel has not given rise to abnormal turbulent flow therein, e.g. because of thrombosis. For this purpose, a measuring probe 4 is installed for measuring flow rate, and then 2048 blood flow measurements are made.

Thereafter, using the mother wavelet $\Psi^{(1)}$, for the values 6, 7, and 8 of the parameter a, the following are determined:
the partition function Z(q,a) such that:

$$Z(q, a) = \sum_{b_i} |T_\Psi[s](b_i, a)|^q$$

where:
s is the signal representing how measurements vary as a function of time;

$T_\Psi[s](b,a) = 1/a \int \bar{\Psi}((x-b)/a) s(x) dx$ and
$\{(b_i,a)\}_i$ is the set of local maxima in T as a function of a;
the spectrum of the function T(q) such that:

$Z(q,a) = a^{\tau(q)}$ in the limit $a \to 0^+$;

the spectrum of the function D(h) such that:

$$D(h) = \min_q (qh - \tau(q))$$

and
the index I(a) that depends on said spectrum, the index being calculated by means of the above-specified formula.

Finally, the average of the indices I(a) is calculated and compared with the threshold of 0.35. If the index is below the threshold, then the flow may be said to be normal. Otherwise, the flow is abnormal.

The graphs of FIGS. 8 to 11 show various steps in this calculation when there is no arterial stenosis, with the index value obtained being 0.19581. In contrast, the similar graphs in FIGS. 12 to 15 represent a case when stenosis is present, since the index is 0.48305. In FIG. 15 it should be observed that the graph has a very steep falling front and a sharp point, which are characteristic of this situation and which are represented by the index.

Figure 8:
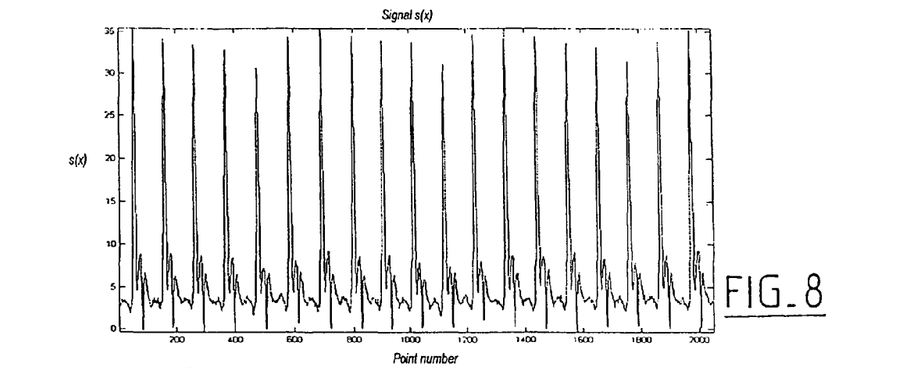
FIGS. 8 to 11 are graphs respectively of a signal s, of partition functions Z(q,a), of the function τ(q), and of the function D(h) during an in vivo experiment in the absence of arterial stenosis.

More precisely FIG. 8 shows the graph of the signal s.

Figure 9:
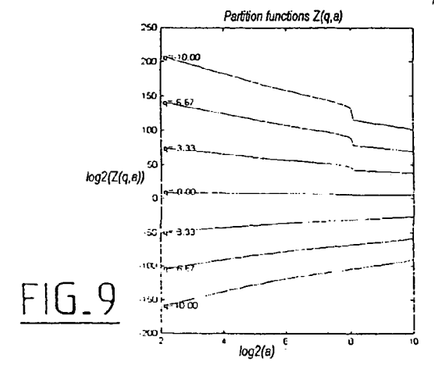
Figure 10:
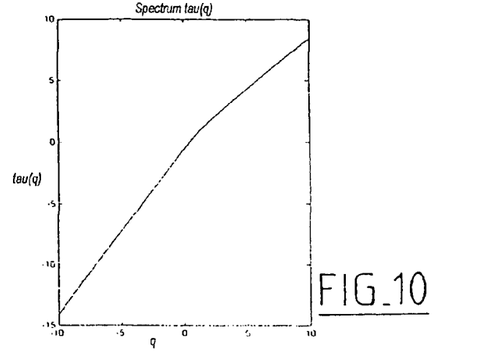
Figure 11:
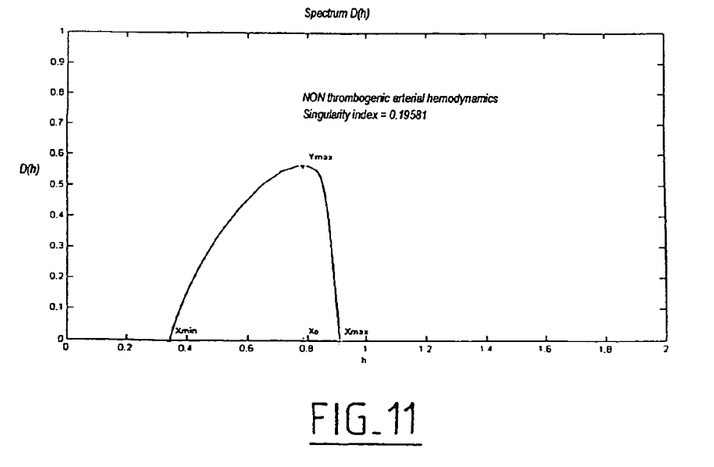
Figure 12:
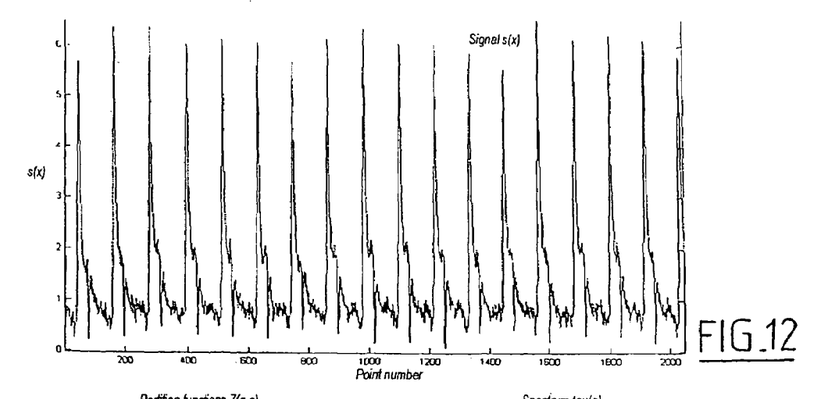
FIGS. 12 to 15 are analogous to FIGS. 8 to 11 for 60% stenosis.

FIG. 9 shows graphs of functions Z(q,a) for a large number of values of a. Similarly, FIG. 10 shows the graphs of spectra $\tau(q)$ taken from the data of FIG. 9. FIG. 11 shows I(a) when a is equal to 8. FIGS. 9 and 10 were implemented to find experimentally which values of the parameter a are the most pertinent, and they are shown here merely to fill out the explanation. (As mentioned above, the values finally selected are a=6, 7, and 8.) In practice, there is no need to plot the curves shown in FIGS. 9 and 10. The algorithm is performed on only three values of a, a=6, 7, and 8, and then the corresponding indices I(a) are averaged and the average is compared with the threshold.

Figure 13:
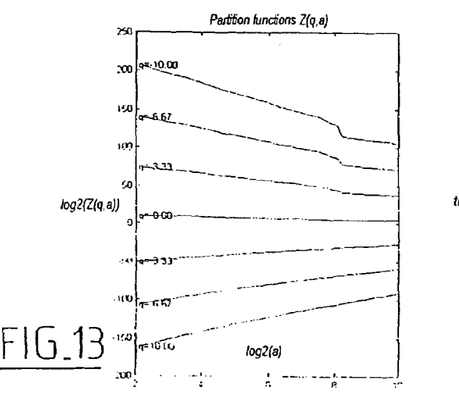
Figure 14:
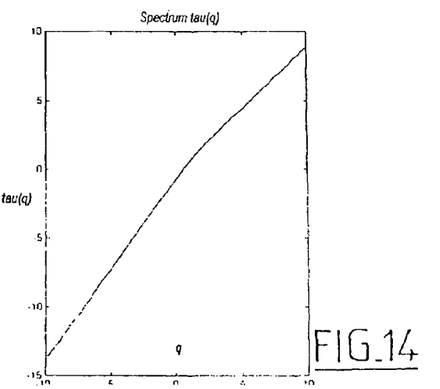
Figure 15:
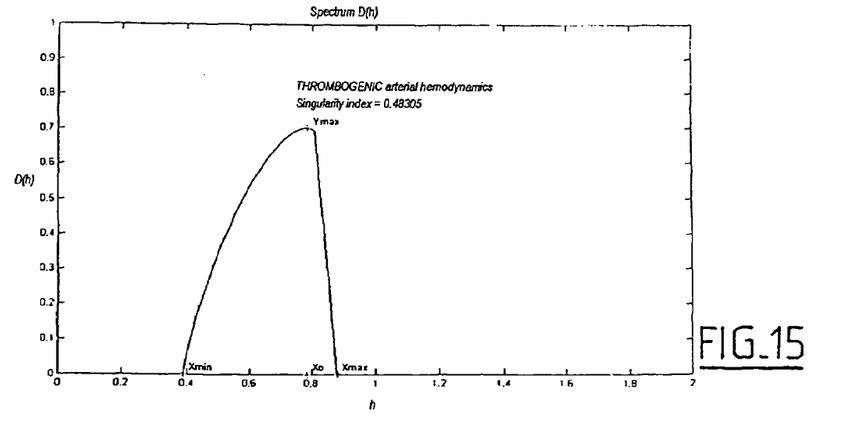

Exactly the same applies to FIGS. 13 and 14 which need not be plotted in practice.

The invention provides numerous advantages:
calculation is performed quickly;
analysis is purely qualitative and thus independent of variations in the recorded magnitude (blood flow rate, speed, pressure, . . . ) and it is independent of the nature of the signal that is recorded;
the measured degree of turbulence is stable, reliable, and reproducible;
the fact that the degree of turbulence is dimensionless means that measurement can be standardized; and
the software script can be stored in a microprocessor, making it possible to increase the speed of execution and to obtain measurements in real time.

There are numerous applications for the invention in the field of medicine:
real time detection, during and/or after an operation, of intravascular formation of thrombi (without restriction on blood vessel calibre) or of thrombus formation, of the degree of turbulence generated by an arterial suture, or of the existence of an intra-arterial stenosis, and with instantaneous calibration thereof;
real time assessment during and/or after an operation of the quality of the hemodynamic repercussions of an arterial suture;
real time assessment during and/or after an operation of the hemodynamic quality of a healthy and/or pathological segment of blood vessel and of the entire accessible arterio-venous network;
real time monitoring of the hemodynamic quality and/or hydrodynamic quality in a circuit for circulation outside the body; and
the probe can be incorporated at the end of an articulated arm of a microsurgical robot, within an endoscope or a celioscope system.

The invention can be implemented in particular in flap surgery which requires numerous arterial and venous sutures.

Other applications of the invention can also be envisaged in numerous disciplines requiring real time detection of variation in the degree of turbulence in a quasiperiodic and/or multifractal one-dimensional signal. A few examples are given below.

In the medical, surgical, or pharmaceutical industries, the invention can be used for designing the hemodynamic properties of intravascular prostheses, for monitoring the effect on blood viscosity of therapeutic molecules, for monitoring hemodynamic modifications caused by next generation intravascular microrobots (nanotechnologies).

In the engineering industry, the invention can be used for monitoring and analyzing vibrations generated in moving parts and can be associated with feedback. The event being monitored is then the movement of the part and the signal used is representative of parasitic displacements due to vibration.

In the automobile industry the invention can be used for monitoring and analyzing the quality (quasiperiodic or turbulent) of oscillation in suspensions and can be used for automatic feedback determining the hardness of a suspension in order to increase ground adherence.

The invention can be used for monitoring and analyzing the quality of the relief (smooth, rough, bumpy) on which the vehicle is travelling. Such monitoring can be performed by scanning the relief ahead of the vehicle. The scanning results in an oscillating signal being transmitted and then received. Analysis of the receive signal makes it possible to anticipate and optimize the adjustment of the suspension.

In general hydrodynamics, the invention makes it easier to monitor qualitatively the flow in pipework, in hoses feeding an engine or a reactor, or monitoring physical magnitudes measured by sensors (lasers) placed in laminar and/or turbulent flows.

In shipbuilding, the invention can be used for monitoring and analyzing the quality (laminar or turbulent) of water flow over zones below the water line: the appearance and/or increase of the phenomenon of cavitation at the surface of the hull and/or of moving parts (propellers). Such monitoring is performed by scanning said underwater surfaces, and in particular the zones thereof where cavitation is generated. This scanning is performed by transmitting an oscillating signal and then receiving it. Analysis of the received signal makes it possible to anticipate and optimize the pitch to which the blades of a propeller are set.

In aviation, the invention can be used for monitoring and analyzing the (laminar or turbulent) quality of layers in the atmosphere in which an aircraft is to travel. This monitoring is performed by scanning atmospheric layers ahead of the aircraft. The scanning is performed by transmitting an oscillating signal and then receiving it. Analysis of the received signal enables the flight plan of the aircraft to be anticipated and optimized.

The invention may be implemented by means of sensors recording changes between laminar and turbulent flows.

It enables explosion levels to be monitored in combustion processes.

In telecommunications, the invention facilitates coding, decoding, and qualitative processing of a low-power signal. In return, such signals require less energy for synthesis and transfer. The invention also makes it possible to perform qualitative decoding of a signal which has lost power. Such qualitative decoding can considerably increase the range between transmission and reception of a signal.

In meteorology, the invention can be used for devising sensors that record variations in atmospheric turbulence.

The invention also has applications in seismology.

Naturally, numerous modifications can be made to the invention without going beyond its ambit. Thus, other formulae can be devised for calculating an index representative of the spectrum of D(h). The invention is applicable to studying flow in a duct that does not form part of a human or animal body.

In addition, color coding can be used to provide visual quantification of the severity of the turbulence corresponding to each zone in which the signal s(x) is recorded on a graph of the signal as displayed together with the results supplied.

In the above embodiments of the invention, processing and analysis of a single signal s(x) is described.

Nevertheless, the invention can be extended to analysis which is simultaneous and/or differed in time and space of a plurality of signals recorded by multiple detectors. A plurality of series of measurements are gathered with each series of measurements forming a signal s(x) which is processed as described above to obtain a singularity index I. The set of singularity indices then constitutes a matrix. The matrix can serve to establish a two-dimensional map (for measurements made in a two-dimensional plane) or a three-dimensional map (for measurements made in three-dimensional space).

What is claimed is:

1. Apparatus for analyzing surgery on a duct forming part of a human or animal body, wherein the apparatus comprises:
   gathering means for gathering at least one series of measurements of a physical phenomenon associated with the surgery or likely to be associated therewith comprising measurements of flow rate for a fluid flowing in the duct; and
   determining means for using a predetermined mother wavelet $\Psi$ to determine for at least one value of a predetermined parameter a:
   the partition function $Z(q,a)$ such that:

$$Z(q, a) = \sum_{b_i} |T_\Psi[s](b_i, a)|^q$$

where:
a is the scale parameter of the wavelet transform and is positive;
q represents the moments of the measure distributed on the wavelet transform modulus maximum (WTMM) tree;
s is a signal representing variation in the measurements of the series as a function of a variable such as time;

$$T_\Psi[s](b, a) = \frac{1}{a} \int \overline{\Psi}\left(\frac{x-b}{a}\right) s(x) dx$$

where $\overline{\Psi}$ is the complex conjugate of the function $\Psi(x)$ in an orthonormal base;
b is a position parameter;
x is a variable in function of which the signal s is recorded; and
$\{(b_i, a)\}_i$ is the set of local maxima in T as a function of a;
the spectrum of the function $\tau(q)$ such that:
$Z(q,a) \approx a^{\tau(q)}$ in the limit $a \to 0^+$;
the spectrum of the function D(h) such that:

$$D(h) = \min_q (qh - \tau(q)) \text{ and}$$

and
an index l(a) depending on said spectrum of the function D(h), which index is calculated by a predetermined formula, index l(a) permitting determination of the level of perturbations in the signal.

2. Apparatus according to claim 1, comprising means for comparing the index l(a) or an average of indices l(a) with a predetermined threshold.

3. Apparatus according to claim 1 wherein the index l(a) is calculated using the formula:

$$l(a) = \frac{y_0}{b+c} + \frac{bc}{y_0(b+c)} + bc - 1$$

in which $$y_0 = \max_x D(x) = D(x_0)$$

$b = x_O - x_{min}$ $c = x_{max} - x_O$.

4. Apparatus according to claim 1, wherein the threshold is equal to 0.35.

5. Apparatus according to claim 1, wherein said determining means are arranged to determine l(a) for at least three values of the parameter a.

6. Apparatus according to claim 5, wherein the at least three values are 6, 7, and 8.

7. Apparatus according to claim 1, wherein the mother wavelet is of the type:

$$\Psi^{(N)}(x)=(d^N/dx^N)e^{-x^2/2}$$

where N is a natural integer.

8. Apparatus according to claim 1, wherein the mother wavelet is $\Psi^{(1)}$.

9. Apparatus according to claim 1, wherein the event is a past event.

10. A method for analyzing surgery on a duct forming part of a human or animal body, the method comprising:

gathering, using a sensor, at least one series of measurements of a physical phenomenon associated with the surgery or likely to be associated therewith comprising measurements of flow rate for a fluid flowing in the duct; and determining, on the basis of a predetermined mother wavelet $\Psi$, at least one value of a predetermined parameter a:

the partition function Z(q,a) where:

$$Z(q,a) = \sum_{b_i} |T_\Psi[s](b_i, a)|^q$$

wherein:

a is the scale parameter of the wavelet transform and is positive;

q represents the moments of the measure distributed on the wavelet transform modulus maximum (WTMM) tree;

s is a signal representing variation in the measurements of the series as a function of a variable such as time;

$$T_\Psi[s](b, a) = \frac{1}{a} \int \overline{\Psi}\left(\frac{x-b}{a}\right) s(x) dx$$

wherein $\overline{\Psi}$ is the complex conjugate of the function $\Psi(x)$ in an orthonormal base;

b is a position parameter;

x is a variable in function of which the signal s is recorded; and $\{(b_i,a)\}_i$ is the set of local maxima in T as a function of a;

the spectrum of the function $\tau(q)$ such that:

$Z(q,a) \approx a^{\tau(q)}$ in the limit $a \rightarrow 0^+$;

the spectrum of the function D(h) such that:

$$D(h) = \min_q (qh - \tau(q))$$

and an index l(a) depending on said spectrum of the function D(h), which index is calculated by a predetermined formula, index l(a) permitting determination of the level of perturbations in the signal.

11. The method of claim 10, further comprising comparing the index l(a) or an average of indices l(a) with a predetermined threshold.

* * * * *